(12) United States Patent
Davies et al.

(10) Patent No.: US 8,298,833 B2
(45) Date of Patent: Oct. 30, 2012

(54) LIQUID BRIDGE AND SYSTEM

(75) Inventors: Mark Davies, Limerick (IE); Tara Dalton, Limerick (IE); Kieran Curran, Limerick (IE)

(73) Assignee: Stokes Bio Limited, Shannon Arms, Limerick (IE)

( * ) Notice: Subject to any disclaimer, the term of this patent is extended or adjusted under 35 U.S.C. 154(b) by 669 days.

(21) Appl. No.: 12/092,261

(22) PCT Filed: Feb. 7, 2007

(86) PCT No.: PCT/IE2007/000013
§ 371 (c)(1), (2), (4) Date: May 20, 2008

(87) PCT Pub. No.: WO2007/091228
PCT Pub. Date: Aug. 16, 2007

(65) Prior Publication Data
US 2008/0277494 A1 Nov. 13, 2008

Related U.S. Application Data

(60) Provisional application No. 60/765,671, filed on Feb. 7, 2006.

(51) Int. Cl.
*G01N 1/10* (2006.01)
(52) U.S. Cl. .............. 436/180; 436/53; 436/52; 422/82; 422/502; 422/501; 422/500
(58) Field of Classification Search .............. 422/67, 422/68.1, 81, 82, 100, 101, 255–257, 500–502, 422/504; 436/52, 53, 174, 180; 9/67, 68.1, 9/81, 82, 100, 101, 255–257; 700/265, 282, 700/283, 285
See application file for complete search history.

(56) References Cited

U.S. PATENT DOCUMENTS 7,235,405 B2   6/2007 Charles et al.
2004/0022686 A1 * 2/2004 Charles et al. ............. 422/82.08
(Continued)

FOREIGN PATENT DOCUMENTS

EP   1 361 442   7/2006
(Continued)

OTHER PUBLICATIONS

International Search Report from WO 2007/091228.
(Continued)

*Primary Examiner* — Jill Warden
*Assistant Examiner* — Cedric Chan

(57) ABSTRACT

A bridge (30) comprises a first inlet port (31) at the end of a capillary, a narrower second inlet port (32) which is an end of a capillary, an outlet port (33) which is an end of a capillary, and a chamber (34) for silicone oil. The oil is density-matched with the reactor droplets such that a neutrally buoyant environment is created within the chamber (34). The oil within the chamber is continuously replenished by the oil separating the reactor droplets. This causes the droplets to assume a stable capillary-suspended spherical form upon entering the chamber (34). The spherical shape grows until large enough to span the gap between the ports, forming an axisymmetric liquid bridge. The introduction of a second droplet from the second inlet port (32) causes the formation of an unstable funicular bridge that quickly ruptures from the, finer, second inlet port (32), and the droplets combine at the liquid bridge (30). In another embodiment, a droplet (55) segments into smaller droplets which bridge the gap between the inlet and outlet ports.

7 Claims, 13 Drawing Sheets

U.S. PATENT DOCUMENTS

2010/0216128 A1    8/2010    Davies et al.

FOREIGN PATENT DOCUMENTS

| | | |
|---|---|---|
| WO | WO 01/01106 | 4/2001 |
| WO | WO2007/091228 | 8/2007 |
| WO | WO2010/133962 | 11/2010 |
| WO | WO2010/133963 A3 | 11/2010 |

OTHER PUBLICATIONS

Written Opinion of the Inerrnational Searching Authority from PCT/IE2007/000013 (8 pages).

PCT/IB2010/001233, "International Search Report" mailed Oct. 22, 2010.

* cited by examiner

Liquid bridge dispensing at three different values capillary radii ratio, $K^*$. (A) $K^* = 0.25$ (B) $K^* = 0.44$ and (C) $K^* = 1.0$ Capillary tip separations are indicated on the images.

Dimensionless plot of dimensionless plug volume, $V*$, versus slenderness ratio, where $\Lambda*$ was $V*$ scaled with $R_2^3$. Results are plotted for $K*$ values of 1.0, 0.44 and 0.25.

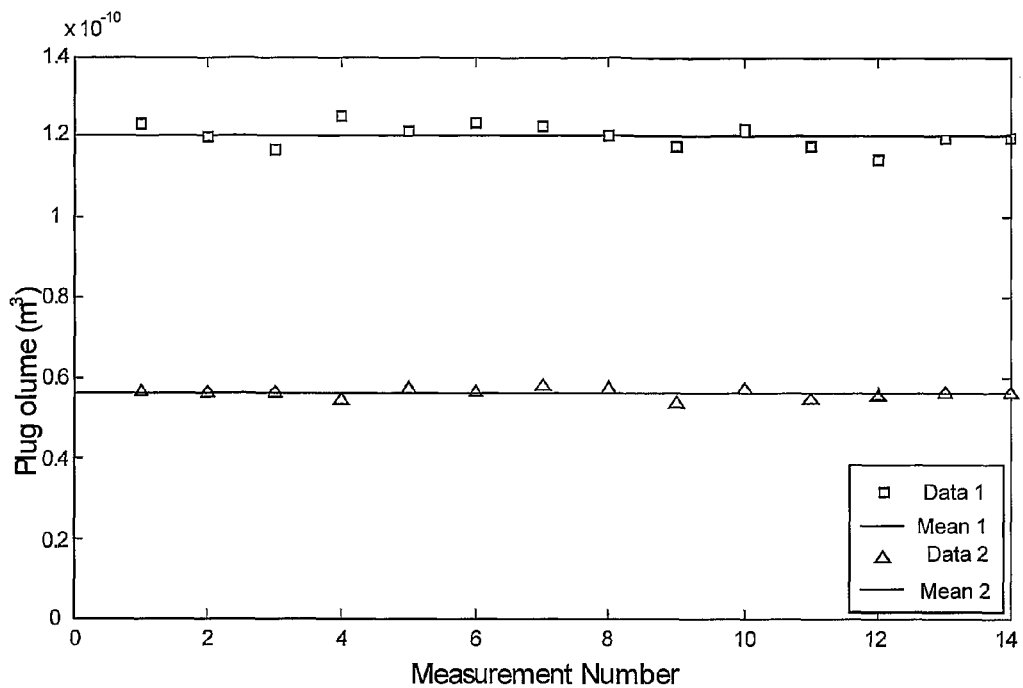

Plug volume variation over fourteen measurements for . $K^* = 0.44$ Horizontal lines represent the mean volume dispensed. The mean plug volumes were approximately 120 nL and 56 nL with maximum variations ±4.46% of and ±3.53% respectively.

Fig.16

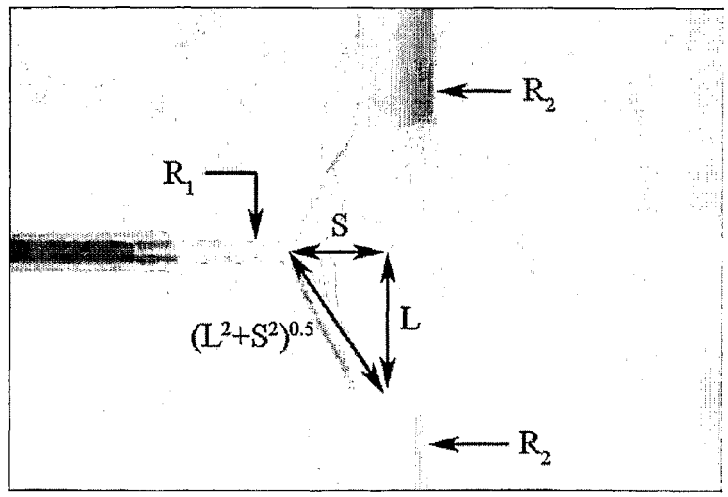

Funicular liquid bridge supported between three capillaries. The geometry used to investigate stability is shown superimposed over the original image.

Fig.17

Experimentally determined stability diagram for a purified water funicular liquid bridge in a density matched silicone oil, Bond number: $1.25 \times 10^{-4}$. Vertical error bars indicate the volumetric ratio uncertainty as a result of camera frame rate.

LIQUID BRIDGE AND SYSTEM

This application is a US national phase of PCT/IE2007/000013, filed on Feb. 7, 2007, which claims priority to U.S. provisional application No. 60/765,671, filed on Feb. 7, 2006.

FIELD OF THE INVENTION

The invention relates to control of liquids at small volumes such as at the microfluidic level.

PRIOR ART DISCUSSION

Microfluidics is a technology which in simple terms refers to the micro-scale devices which handle small volumes of fluids—as small as micro-, nano- and pico- and femtolitre volumes. Microfluidic devices have dimensions ranging from several millimetres to micrometers. Typically dimensions of the device are measured in micrometers. Given the small dimensions of microfluidic devices or components thereof, not surprisingly microfluidic devices require construction and design which differ from macro-scale devices. Simple scaling down in size of conventional scale devices to microfluidic scale is not a simple option. Liquid flow in microfluidic devices differs from that of macro-scale size devices. Liquid flow tends to be laminar, surface flux and surface tension start to dominate and as a result effects not seen at the macro level become significant. At the microfluidic level other differences include faster thermal diffusion, predominately laminar flow and, surface forces are responsible for capillary phenomena and an electric double layer (EDL).

Because microfluidics can accurately and reproducibly control and dispense minute volumes of fluid—in particular volumes less than one µl. The application of microfluidics can have significant cost-saving potential. The use of microfluidics technology can potentially reduce cycle times, shorten time-to-results and increase throughput. Furthermore incorporation of microfluidics technology can, in theory, enhance system integration and automation.

Heretofore, handling of small quantities of liquids being transferred from one device or conduit to another often involves pipetting, which is a time-consuming manual procedure.

US2005/0092681 describes a device for mixing liquids by transporting them to a confluent portion. US2005/0272144 discloses user of a mixing flow path for diffusion and mixing of liquids.

The invention is directed towards achieving improved liquid control in microfluidic systems.

SUMMARY OF THE INVENTION

In this specification the term "droplet" is used to mean a small quantity or plug of liquid as it flows in an immiscible carrier liquid along a conduit.

According to the invention, there is provided a liquid bridge comprising:
- at least one inlet port for delivery of a liquid A and an immiscible carrier liquid B,
- at least one outlet port,
- a chamber within which the ports are located, the chamber having a capacity such that it fills with carrier liquid B to fill the space between an inlet port and an outlet port; and
- wherein the ports are mutually located and have dimensions such that liquid A periodically bridges to the outlet port due to fluidic instability and droplets are periodically delivered to the outlet port.

In one embodiment, the liquid bridge comprises at least two aligned inlet and outlet ports for droplet formation during flow of liquid from one port to the other.

In one embodiment, the ports have a width dimension in the range of 150 µm to 400 µm.

In one embodiment, the ports are circular in cross-section and said dimension is diameter.

In one embodiment, at least one port is provided by an end of a capillary tube.

In one embodiment, the separation of an inlet port and a corresponding outlet port is in the range of 0.2 mm and 2.0 mm.

In one embodiment, said separation is approximately 1.5 mm.

In another embodiment, the conduit and the ports allow passage of a carrier liquid B having a viscosity in the range of 0.08 Pas and 0.1 Pas.

In one embodiment, the bridge comprises at least first and second inlet ports arranged for delivery of inlet liquid droplets and an output port for outlet of a mixed liquid droplet.

In one embodiment, the first inlet port and the outlet port are co-axial and the second inlet port is substantially perpendicular to their axis.

In a further embodiment, the distance between the second inlet port and the axis of the co-axial ports is in the range of 1.0 mm to 2.0 mm.

In one embodiment, the second inlet port has a smaller cross-sectional area than the first inlet port.

In one embodiment, an inlet port is arranged relative to an outlet port for mixing of droplets of liquid A arriving at said inlet port by collision within the chamber.

In another aspect, the invention provides a liquid bridge system comprising any liquid bridge as defined above, and a flow controller for controlling flow of liquids A and B to the bridge and operation of the bridge according to droplet formation characteristics.

In one embodiment, the controller directs flow of carrier liquid B at a flow rate in the range of 2 µl/min and 5 µl/min.

In one embodiment, the controller directs pressure in the chamber to be in the range of 0.5 bar and 1.0 bar above atmospheric.

In one embodiment, a droplet formation characteristic is a plot of volumetric ratio vs. droplet slenderness.

In a further embodiment, a droplet formation characteristic is capillary separation.

In one embodiment, a droplet formation characteristic is droplet volume vs. slenderness ratio.

In one embodiment, a droplet formation characteristic is $V^*(Q^*)$ versus $\Lambda^*$ In one embodiment, a droplet formation characteristic is ratio of capillary diameters.

In one embodiment, the carrier liquid B is oil.

In another embodiment, the controller comprises means for filling the chamber with carrier liquid B which is density matched with the liquid A such that a neutrally buoyant environment is created within the chamber.

In one embodiment, the carrier liquid B has characteristics causing the droplets in the chamber to have a spherical shape between an inlet port and an outlet port.

In one embodiment, the density of the carrier liquid B and the cross-sectional areas of the ports are such that the carrier liquid B flows and surrounds the droplets of liquid A in the outlet port.

In one embodiment, the velocity profile across the outlet port is such as to cause internal movement within droplets of liquid as they flow from an outlet port.

In one embodiment, said internal flow is internal circulation.

In one embodiment, the carrier liquid B forms a protective film which is static very close to the internal surface of an outlet port and flows with the droplets further from the said surface.

In one embodiment, a droplet formation characteristic is volumetric ratio vs. funicular slenderness.

In one embodiment, the arrangements of the ports and the properties of the carrier liquid B are such as to cause segmentation of liquid A into a plurality of outlet droplets.

In a further aspect, the invention provides a method of controlling operation of any liquid bridge as defined above, the method comprising directing flow of liquids A and B into the bridge with flow characteristics determined according to the geometry of the bridge ports and their separations and according to liquid properties, such that liquid A periodically bridges to the outlet port due to fluidic instability and droplets are periodically delivered to the outlet port.

In one embodiment, the flow is controlled to cause segmentation of a continuous stream or large droplets of the liquid A in the chamber to provide a sequence of segmented droplets derived from the inlet liquid A.

In one embodiment, different, miscible, liquids A and C are delivered to the bridge, and flow is controlled so that droplets of liquids A and C mix within the chamber.

In one embodiment, the liquids A and C are delivered to different inlet ports of the bridge, said ports being located so that droplets of liquids A and C mix to form a single droplet which exits via the outlet port.

In one embodiment, the liquids A and C are delivered to the bridge in a single inlet port as successive droplets, and flow is controlled so that the droplets collide within the chamber to mix.

In one embodiment, the method comprises withdrawing carrier liquid B from between said droplets before they enter the bridge so that they are caused to collide within the chamber.

In one embodiment, the liquids A and C comprise different chemical species contained within an aqueous phase.

In one embodiment, the carrier liquid B has a viscosity in the range of 0.08 Pas and 0.1 Pas.

In one embodiment, the carrier liquid B flows into the bridge at a flow rate in the range of 2 µl/min and 5 µl/min.

In one embodiment, the carrier liquid B is density matched with the liquid A such that a neutrally buoyant environment is created within the chamber.

In one embodiment, the carrier liquid B has characteristics causing the droplets in the chamber to have a spherical shape between an inlet port and an outlet port.

DETAILED DESCRIPTION OF THE INVENTION

Brief Description of the Drawings

The invention will be more clearly understood from the following description of some embodiments thereof, given by way of example only with reference to the accompanying drawings in which:—

FIGS. 15 and 16 are further characteristic plots for a liquid bridge segmentor;

FIG. 17 is a photograph of a funicular bridge, also showing dimension parameters;

DESCRIPTION OF THE EMBODIMENTS

Figure 1:
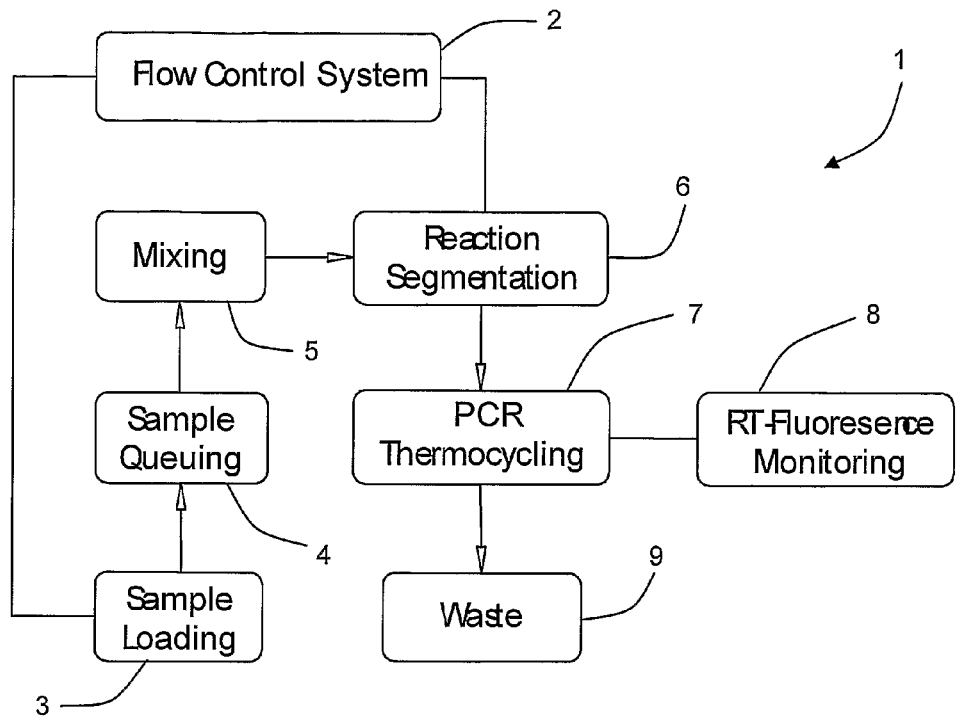
FIGS. 1 and 2 are schematic diagrams of a PCR preparation microfluidic system of the invention.
Figure 2:
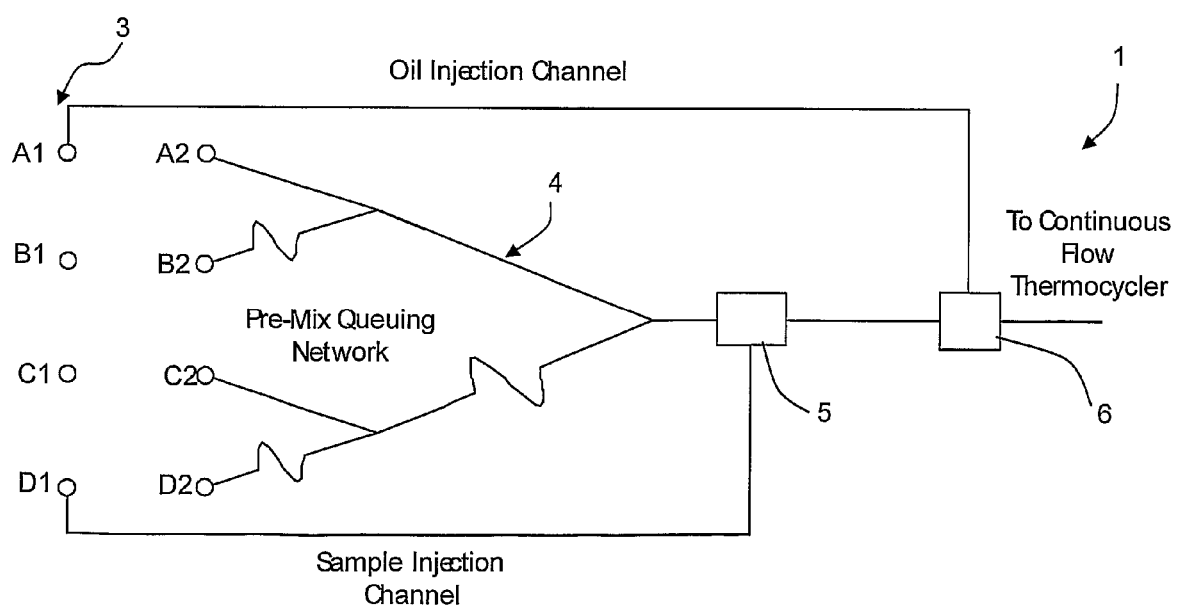

Referring to FIGS. 1 and 2 a microfluidic preparation system 1 for a Polymerase Chain Reaction ("PCR") system is shown at a high level. It comprises components 2-9 for, respectively flow control, sample loading, sample queuing, mixing, reaction segmentation, PCR thermocycling, RT fluorescence monitoring, and waste handling.

The system 1 is operated to find the gene expression profile of a patient sample using the PCR technique. Standard scientific protocols are available on the extraction and purification of mRNA and the subsequent production of cDNA. This is then mixed with the specific primers and the general other reagents prior to amplification.

In the simple example illustrated sample streams of droplets A2, B2, C2, and D2 are managed in the queuing network 4 so that the order in which they are delivered to the mixer 5 is controlled as desired. For example, there may be a long sequence of droplets of type A2, followed by equivalent streams for B2, C2, and D2. Alternatively, there may be repeated sequences of A2, B2, C2, and D2, the droplets being interleaved in the queuing network 4. The mixer 5 joins together a droplet of sample type D1 and each particular droplet which passes through the mixer 5. The chemical composition of the droplets is not the subject of this invention, suffice to say that they are chosen according to the particular PCR experiment being run. The invention applies particularly to the manner in which the droplets are mixed by the mixer 5 to provide micro reactor droplets. It also applies to the manner in which a long stream of a sample is broken up into a sequence of droplets of a particular size by the segmentor 6. These droplets are separated by an enveloping carrier liquid, in this case oil A1 delivered to the segmentor 6.

Thus, the system 1 achieves automation of the production of liquid droplets in a carrier fluid with the sample, primers and reagents mixed. Take for example a situation where there are N genes, each interrogated m times. To increase the experimental certainty, there may be m×N droplets. There will also be p housekeeping genes and q negative controls. The total number of droplets, M, may be calculated by:

$$M=(m \times N)+p+q.$$

This may be of the order of 400 droplets.

Liquid bridges are used to mix the reagents and segment droplets in the components 5 and 6. These generate a line of droplets carrying a variety of different chemistries. The choice of fluid properties will be described so that a liquid film is always present between the droplet and the channel wetted surfaces. This has the dual effect of preventing carry-over contamination and surface inhibitory effects that restrict amplification.

A typical Q-PCR reaction contains: fluorescent double-stranded binding dye, Taq polymerase, deoxynucleotides of type A, C, G and T, magnesium chloride, forward and reverse primers and patient cDNA, all suspended within an aqueous buffer. Reactants, however, may be assigned into two broad groups: universal and reaction specific. Universal reactants are those common to every Q-PCR reaction, and include: fluorescent double-stranded binding dye, Taq polymerase, deoxynucleotides A, C, G and T, and magnesium chloride. Reaction specific reactants include the forward and reverse primers and patient cDNA.

In more detail, the following describes the components 2-8.

2: A flow control system consisting of a precision pump with a motor controlled drive that regulates the flow rates used to load and drive samples through the system.

3: Sample loading is accomplished by infusing oil into small wells. These wells contain the universal reactants for each PCR reaction in addition to specific primers. Each well contains a different primer set to quantify specific gene expression levels. The samples exit the wells as long microfluidic plugs.

4: The loading process is followed by sample queuing where the reactants flow through a network such that they are arranged serially or alternatively as desired in a tube.

5: The reactants then flow through the mixer where they are combined with the final PCR reactant, the patient cDNA. The production of negative reactants, containing no patient cDNA, is also possible during this process.

6: The relatively large reaction plugs are then segmented into smaller plugs or droplets in a liquid bridge segmentation process. This is performed to reduce experimental uncertainty.

Figure 3:
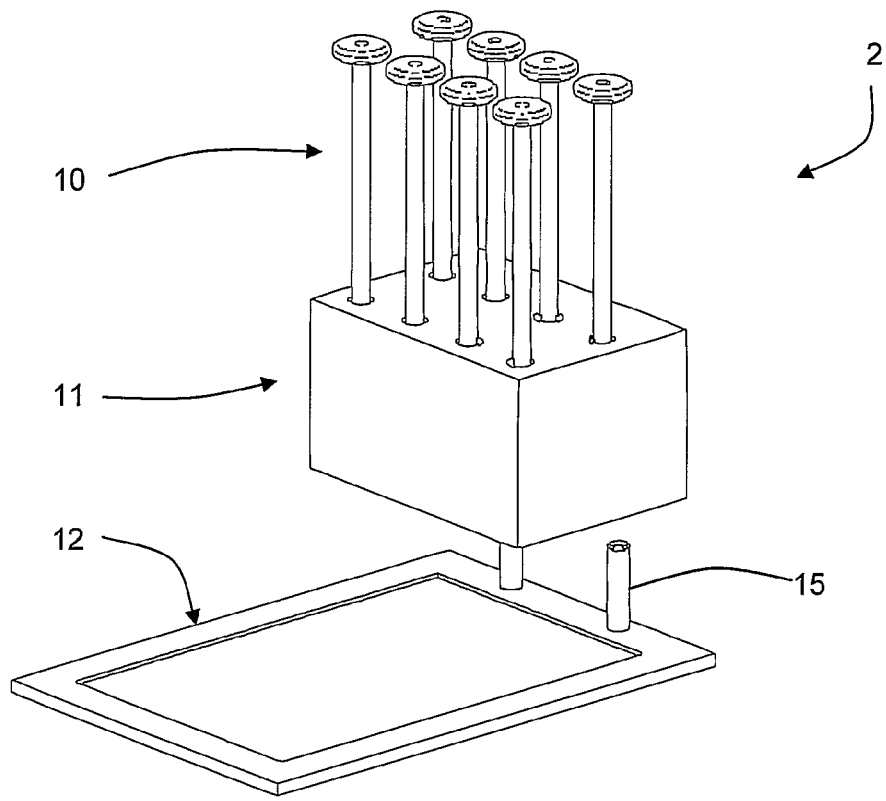
FIGS. 3 and 4 are above and beneath perspective views of a pumping system of the microfluidic system.
Figure 4:
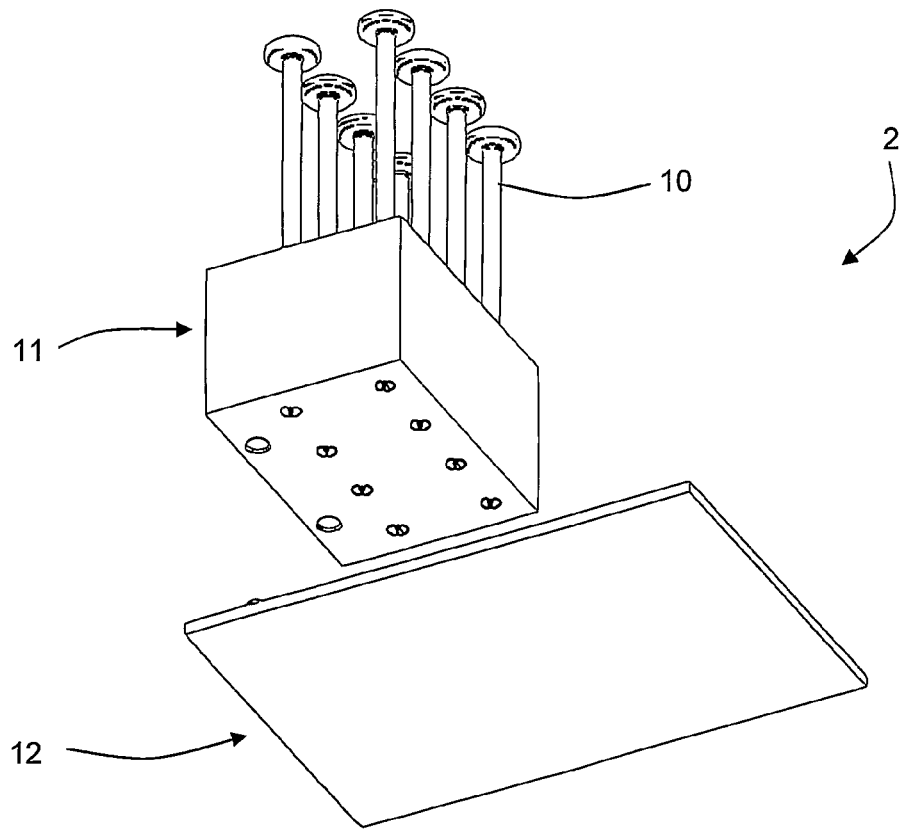
Figure 5:
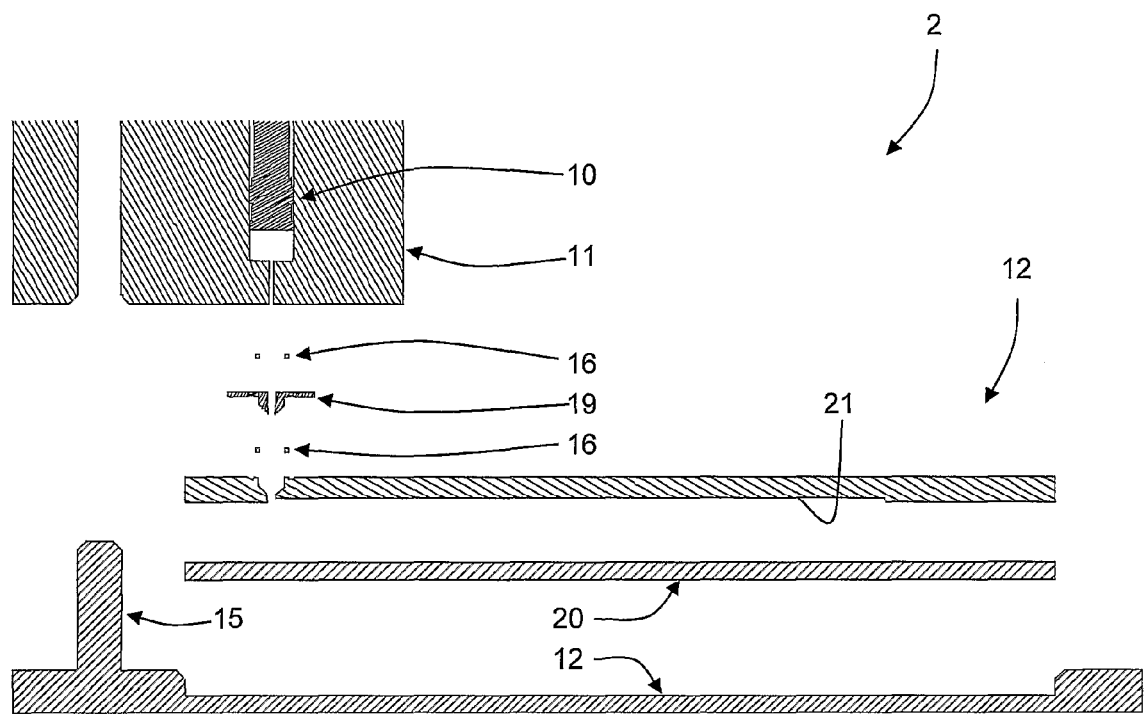
FIG. 5 is a cross-sectional diagram illustrating a sample well of the pumping system in more detail.

Referring also to FIGS. 3 to 5, the wells labelled A1, A2, B1, B2, etc. in FIG. 2 connect directly to the flow control system 2, as shown in FIG. 3. The system 2 consists of eight Teflon-tipped plungers 10 each inserted into a 686 μl cylinder in a polycarbonate infusion manifold 11 filled with silicone oil. There is a substrate microchannel 21 formed between the manifold 11 and a cradle 12. The plungers 10, when driven at a constant velocity, pump the oil from the infusion manifold 11 through the sample wells and into the substrate microchannels. The flow rates are maintained equal in each well so that the queuing of droplets only depends upon path length. The locations of the ports are shown in FIG. 4. They connect directly to opposing substrate wells.

The plungers are driven by a pusher block (not shown) on a lead-screw connected to a stepper motor to infuse silicone oil at equal flow rates into each sample well to pump the contents of the wells into microchannels. This method of pumping could also be done from a reservoir, possibly with internal baffling to equalise the flow. In this case only a single plunger would be necessary.

The sample wells may be either integrated on disposable substrates or connected via polycarbonate sample well strips on non-disposable versions. Alignment dowels 15 are used to position the wells accurately under the infusion manifold 11. Sealing between mating components is ensured with the use of elastomer gaskets 16 on each side of a sample well strip 19.

The gaskets provide a liquid-tight seal with the application of a constant upward force to the substrate cradle 12 and a sealing sheet 20. The substrate measures 70 mm×90 mm in this embodiment. When an upward force is applied to the substrate cradle, a liquid tight seal is formed between the infusion manifold, sample well strip and the microchannel substrate with the aid of elastomer gaskets at mating interfaces.

As silicone oil is pumped by the plungers 10 it passes through the wells 19 into which samples have been loaded. Thus, the flow into each microchannel 21 is a stream of carrier oil and sample droplets for entry into the queuing network 4.

Differences in microchannel path lengths delay the arrival of sample droplets to the outlet of the queuing network 4. It can be seen from FIG. 2, that the shortest path length exists from well A2 to the network outlet. The next shortest path length exists from well B2 to outlet and so on. The result of the queuing network is a linear array of reaction droplets separated by silicone oil. This queuing network design has the additional benefit of being scalable to array many samples.

Figure 6:
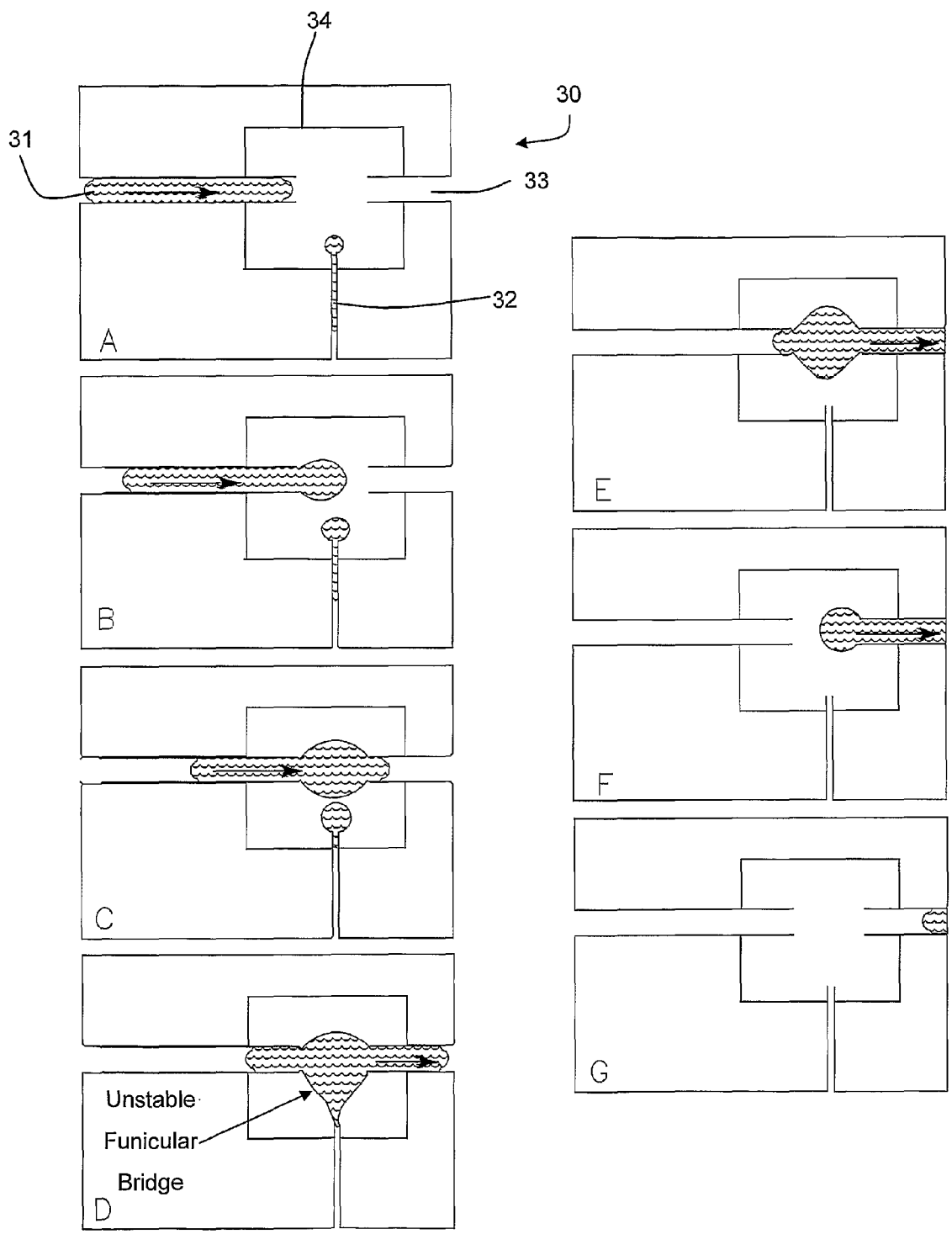
FIG. 6 is a sequence of diagrams A to G illustrating operation of a mixing bridge incorporating a funicular bridge.

The aqueous phase reaction droplets are combined with patient cDNA at the mixer 5. The two-phase nature of microfluidic flow necessitates a means of combining fluids. The fluids are combined into a single droplet in the mixer 5 by virtue of funicular bridge instability. FIG. 6 shows funicular bridge mixing in a particular funicular bridge 30 of the mixer 5. The bridge 30 comprises a first inlet port 31 at the end of a capillary, a narrower second inlet port 32 which is an end of a capillary, an outlet port 33 which is an end of a capillary, and a chamber 34 for silicone oil. Initially, the entire system is primed with a density matched oil. The inlet and outlet ports 31 and 33 are of diameter 200 μm, more generally preferably in the range of 150 μm to 400 μm. The separation of the ports 31 and 33 is c. 1 mm, and the distance between the second inlet port 32 and the axis of the ports 21 and 33 is c. 1.5 mm. The chamber 34 is 5 mm in diameter and 3 mm in depth. The enveloping oil provides a pressure of no more than 0.5 to 1.0 bar above atmospheric. It has a viscosity of 0.08 to 0.1 Pas, and the flow rate is in the range of 2 to 5 μl/mn The oil is density-matched with the reactor droplets such that a neutrally buoyant environment is created within the chamber 34. The oil within the chamber is continuously replenished by the oil separating the reactor droplets. This causes the droplets to assume a stable capillary-suspended spherical form upon entering the chamber 34, steps B and C. The spherical shape grows until large enough to span the gap between the ports, forming an axisymmetric liquid bridge.

The introduction of a second droplet from the second inlet port 32 causes the formation of an unstable funicular bridge that quickly ruptures from the, finer, second inlet port 32, causing all the fluid to combine at the liquid bridge 30.

The sequence of illustrations A to G in FIG. 6 show how the enveloping liquid controls droplet formation and mixing according to surface tension. The pressure in the chamber 34 is atmospheric. The interfacial tension within the chamber 34 is important for effective mixing. Also, the relative viscosity between the aqueous and oil phases is important. The internal pressure (Laplace pressure) within each droplet is inversely proportional to the droplet radius. Thus there is a higher internal pressure within the droplet at the second inlet port 32. Because they are of the same phase, there is little interfacial tension between the large and small droplets, and the internal pressures cause a joining of the droplets, akin to injection of one into the other. Also, physical control of the locations of the droplets is achieved by the enveloping oil, which is of course immiscible with the droplets. Further addition of a surfactant to either phase can change the interfacial tension.

Figure 7:
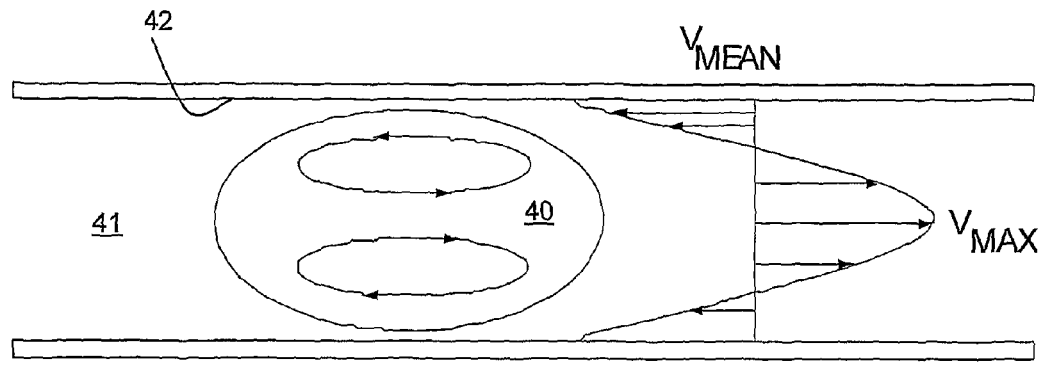
FIG. 7 is a diagram showing internal circulation and the protective oil film around a micro-reactor droplet.

FIG. 7 shows the internal circulation that takes place within a flowing droplet 40 carried by an immiscible oil 41. The velocity profile on the right shows the velocity distribution within the plug relative to the average velocity of the flow. This internal circulation causes excellent mixing and enhances chemical reactions within the droplet 40, and hence it may be regarded as a micro-reactor. The location of a protective oil film 41 is also shown, separating the droplet 40 from the channel walls 42 in addition to separating the droplets 40 from each other. The patterns observed may be visualised if the observer adopts a reference frame that moves at the mean velocity of the flow. With this in mind, the flow can be imagined as a fast moving fluid along the centre-streamline toward the leading face of the plug. Fluid is then circulated back to the rear of the plug near the walls of the microchannel. Internal circulation within flowing microfluidic plugs is a powerful mixing mechanism that, in contrast to existing three dimensional serpentine micromixers, does not require complex microchannel geometries. Homogenous mixing is known to increase reaction kinetics and internal circulation is an important advantage of the two-phase plug flow regime. The establishment of internal circulation and protective films is enhanced by the use of circular polymeric microchannels, specifically FEP fluorocarbon polymeric microchannels. This mechanism enhances mixing within a droplet downstream of the mixer 5.

Figure 8:
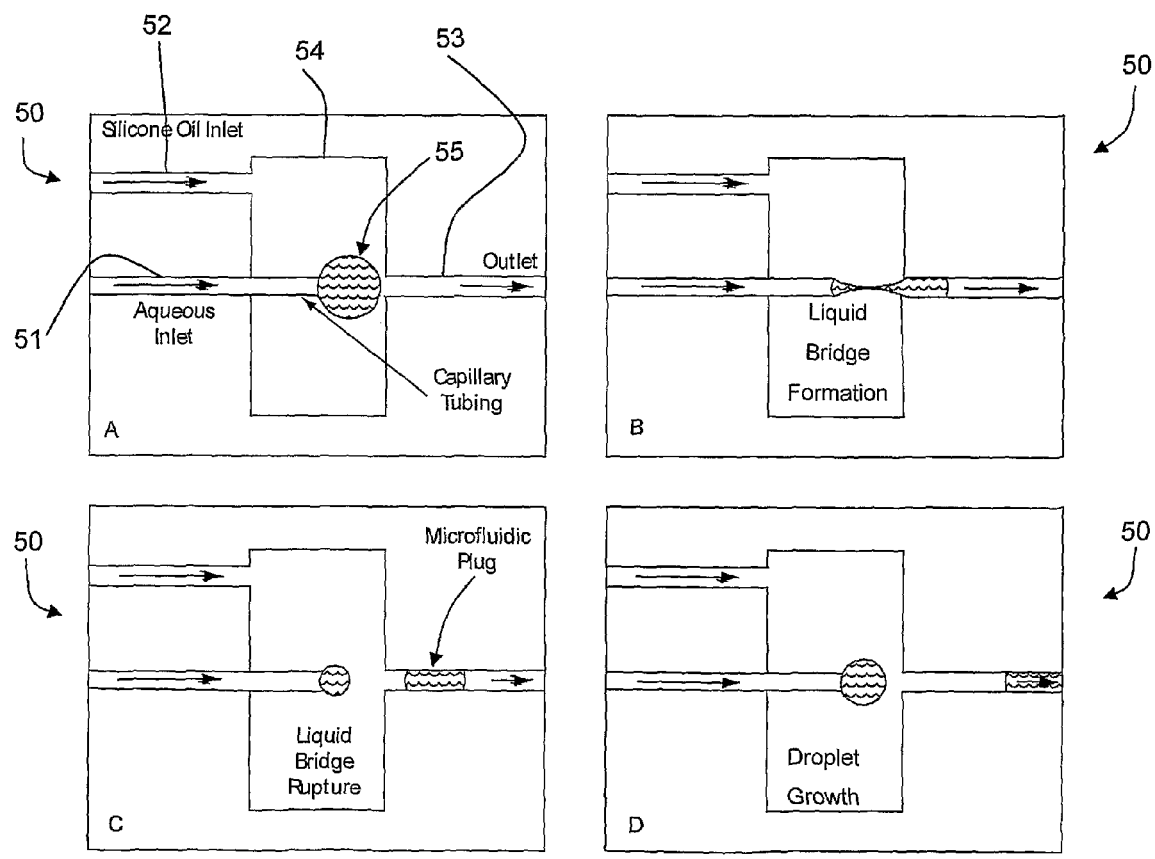
FIG. 8 is a sequence of diagrams A to D illustrating operation of a segmentation bridge.

Fully mixed plugs then enter the segmentor 6 to split master reaction plugs into four smaller droplets, containing identical chemistries that are individually monitored during thermocycling. This step reduces experimental uncertainty. A bridge 50 of the segmentor 6 is shown in FIG. 8. The bridge 50 comprises an aqueous inlet 51, an oil inlet 52, an outlet 53, and a chamber 54. The chamber 54 is 5 mm in diameter and 3 mm in depth and the internal pressure caused by flow of silicone oil is no more than 0.5 to 1.0 bar above atmospheric. The diameter of the ports 51 and 53 is 200 µm, and is more generally preferably in the range of 150 µm to 400 µm. The spacing between the ports 51 and 53 is 0.5 mm, and is more generally preferably in the range of 0.2 to 1.0 mm. The outlet flow rate from the segmentor is 5 µl/min, more generally in the range of 2 to 8 µl/min.

The liquid bridge's geometry and the enveloping carrier liquid create a periodic instability between the opposing ports 51 and 52 due to surface tension. A droplet 55 is initially formed at the end of the inlet port 51 (diagram A). As shown in diagram B the droplet liquid then momentarily bridges the ports 51 and 53. The volume held in this bridge is then steadily reduced by the action of the silicone oil inlet. This causes the formation of an unstable liquid bridge that ruptures to release a smaller plug at the outlet. When the inlet oil flowrate matches the aqueous droplet flowrate, smaller segmented droplets, separated by the same volume of silicone oil, are produced by this bridge. The segmenting mechanism reliably produces uniform aqueous plugs separated by oil that do not rely on the shear force exerted by the carrier fluid.

Multiple dispensing bridges with N inputs 51 and N outputs 53 are also provided. In this case multi lumen tubing may be used as a conduit to carry fluid from the preparation system through the continuous flow PCR thermocycler. Multi lumen tubing contains many micro-bores such that each bore represents a fluid path through which PCR thermocycling may occur.

Figure 9:
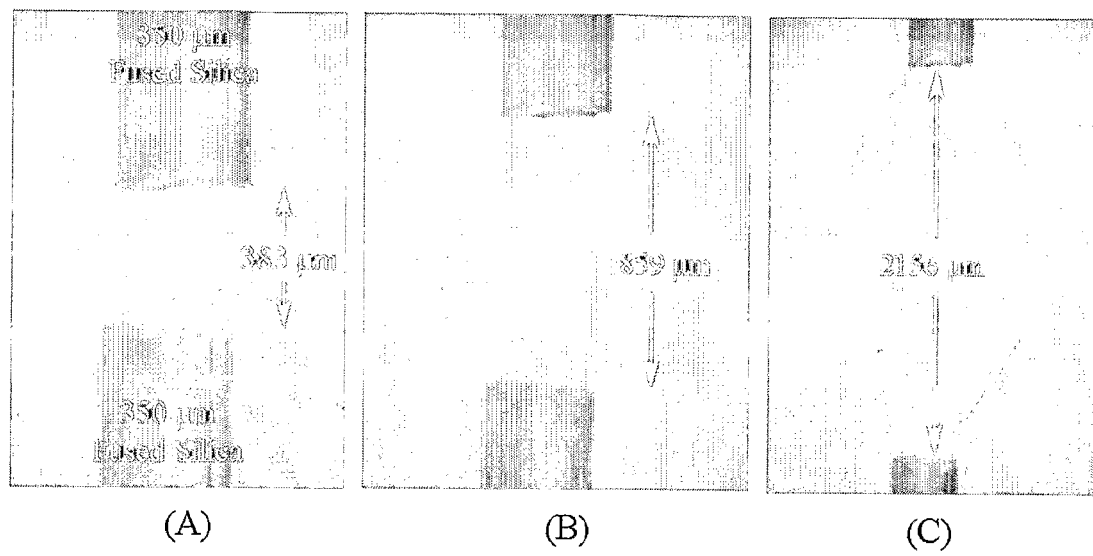
FIG. 9 is a sequence of photographs showing liquid dynamics and dimensions at a liquid bridge.

Liquid bridge stability was studied as a means to predicting the geometric conditions at which rupture occurs. Liquid bridge rupture may be defined as the complete breakage of the liquid filament connecting one solid support to the other. The dimensionless parameters characterising liquid bridges are used to define the stability boundary at which rupture was observed. FIG. 9 presents images of liquid bridges at three slenderness conditions just prior to rupture. The rupture was caused by the withdrawal of liquid bridge fluid from one capillary tube. It was observed that low slenderness ratio liquid bridges, an example of which is shown in FIG. 9 (A), adopt a thimble shape at the minimum volume stability. Larger slenderness ratio liquid bridges, such as that shown in FIG. 9 (C), possess a barrel form with a maximum radius at the bridge mid-span. Intermediate slenderness ratios were found to have a near cylindrical shape at the minimum volume stability limit. Images (A), (B) and (C) of FIG. 9 show liquid bridges with slenderness ratios of 1.09, 2.45 and 6.16 respectively.

Figure 12:
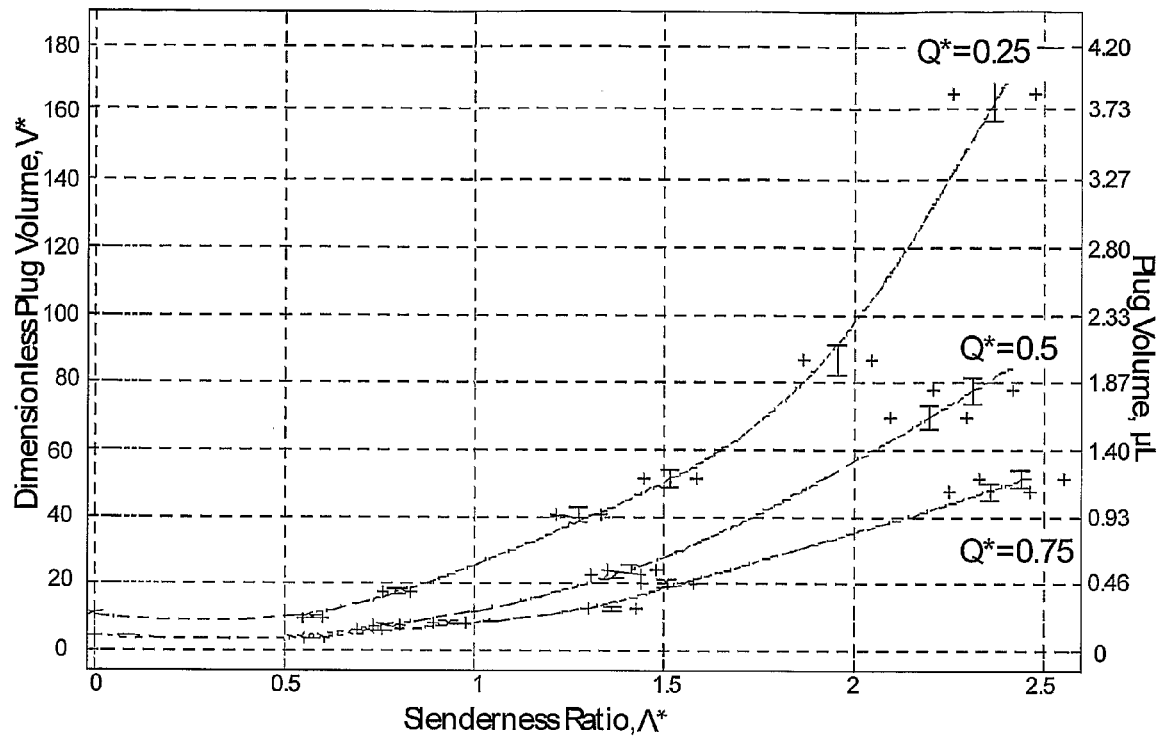
FIG. 12 is a characteristic plot for a liquid bridge segmentor.

The stability of liquid bridges was examined as a function of slenderness, $\Lambda^*$, which is the ratio of tip separation, L, to the mean diameter, $2R_0$, of the supporting capillaries, i.e. $\Lambda^*=L/2R_0$. Stability was also investigated as a function of volumetric ratio, $V^*$, which is the ratio of liquid bridge volume to the volume of a cylinder with a radius $R_0$, the average radius of the supporting capillaries, i.e. $V^*=V/(\pi R_0^2 L)$. The location of the stability boundary, or rupture point, was determined experimentally by fixing the slenderness, establishing a stable liquid bridge between capillary tips and withdrawing fluid from one capillary until rupture was observed. A digital image of the liquid bridge just prior to rupture was then analysed, using an edge detection measurement technique to determine the total volume and hence the volumetric ratio, $V^*$. The slenderness was then adjusted and the experiment repeated. $K^*$ represents the ratio of the radius of the smaller disk, $R_1$, to the radius of the larger one, $R_2$, that is $K^*=R_1/R_2$. FIG. 12 shows the approximate location of the minimum volume stability boundary for liquid bridges with a lateral Bond number of $1.25 \times 10^{-4}$, a near weightless environment. Vertical and horizontal error bars indicate experimental uncertainty.

Figure 10:
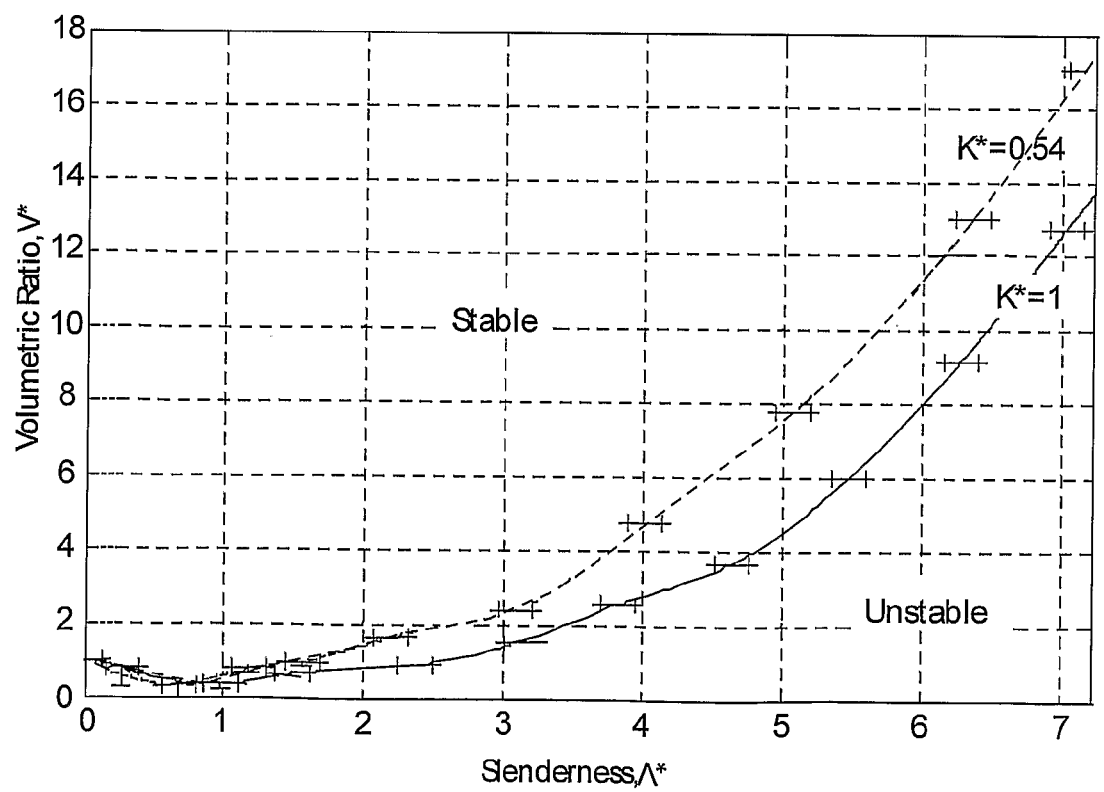
FIG. 10 is a diagram showing a characteristic plot of volumetric ratio vs. slenderness at a liquid bridge for segmentation.

At high volumetric ratios, FIG. 9 (C) for example, bridges maintain their integrity and reach a minimum energy configuration. At low volumetric ratios, FIG. 9 (A) for example, the bridges break before the interfacial energy is minimized. The initial dip in the stability boundary at low slenderness ratios is caused by low-volume droplets not fully wetting the exposed fused silica of the capillary tips. The influence of unequal capillaries on the $\Lambda^*-V^*$ stability diagram is also shown in FIG. 10. It can be seen that the unstable region of the $\Lambda^*-V^*$ plane increases as the parameter $K^*$, the ratio of capillary radii, decreases. The results presented in FIG. 10 confirmed that the static stability of liquid bridge is purely geometrical at low Bond numbers. It is notable that low slenderness ratio bridges are almost completely stable, with respect to rupture, for all capillary radii measured. Rupture was observed only at very low volumetric ratios with the liquid bridge assuming a thimble shape. Liquid bridge instability when applied to fluid dispensing is particularly useful as a replacement for microchannel shear-based dispensing systems. In more detail, FIG. 10 shows an experimentally determined stability diagram for a de-ionized water liquid bridge in a density matched silicone oil, Bond number: $1.25 \times 10^{-4}$. Vertical error bars indicate the volumetric ratio uncertainty as a result of camera frame rate. Horizontal error bars indicate slenderness uncertainty due to capillary tip misalignment. The parameter $K^*$ is the ratio of supporting capillary radii.

The following describes the use of liquid bridge instability as a mechanism for dispensing sub-microlitre volumes of fluid in a continuous manner. The approach uses the liquid bridge's dependence on geometry to create a periodic instability between opposing capillary tips. The dispensing mechanism provides a reliable means of producing uniform aqueous plugs separated by silicone oil that did not rely on the shear force exerted by the carrier fluid. The repeatability with which the method can dispense plugs is examined. The approach uses the liquid bridge's dependence on geometry to create a periodic instability between opposing capillary tips. A stable liquid bridge is first established between aqueous inlet and outlet. The volume held in this bridge is then steadily reduced by the action of the silicone oil inlet. This causes the formation of an unstable liquid bridge that ruptures to release a smaller plug at the outlet. The segmenting mechanism provides a reliable means of producing uniform aqueous plugs separated by silicone oil that does not rely on the shear force exerted by the carrier fluid. Furthermore, a protective oil film is established between the walls of the circular capillaries and the droplet to prevent carryover contamination.

Figure 11:
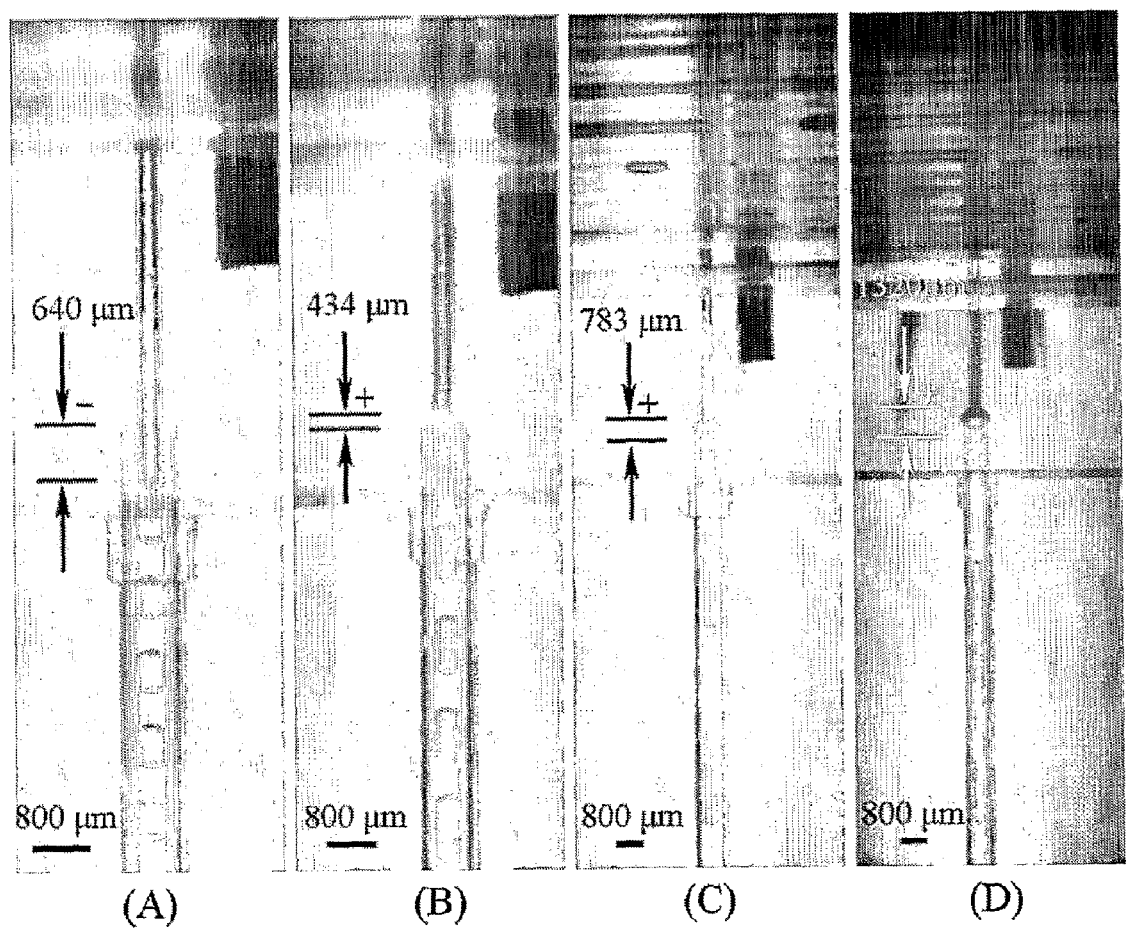
FIG. 11 is a set of photographs of liquid bridge segmentors having different geometries.

FIG. 11 (A)-(D) presents images of liquid bridge dispensing at four different slenderness ratios. (A) $\Lambda^*=0$, (B) $\Lambda^*=0.76$, (C) $\Lambda^*=1.37$ and (D) $\Lambda^*=2.31$. $Q^*=0.5$, $K^*=0.44$. Increasing the capillary tip separation, and hence the slenderness ratio increases the plug volumes dispensed. $Q^*$, the oil flowrate as a fraction of the total flowrate, was maintained constant at 0.5. Image (A) shows dispensing with the dispensing capillary inserted inside the outlet capillary. This configuration was assigned a slenderness ratio, $\Lambda^*$, of zero. Slenderness ratios close to zero resulted in the smallest volume plugs dispensed for this geometry. The effect of increasing tip separation on dispensed plug volume is shown in FIG. 11 (B)-(D). Increasing tip separation, i.e. slenderness ratio, resulted in larger volume aqueous plugs punctuated by approximately the same volume of silicone oil. This was due to the silicone oil inlet flowrate being maintained constant and equal to the aqueous droplet inlet flowrate.

FIG. 12 presents a plot of $V^*$, against slenderness ratio, $\Lambda^*$, where $V^*$ is the dimensionless plug volume scaled with $R_0$, i.e. $V^*=V/R_0^3$. Results are presented for three different values of the oil flowrate fraction, $Q^*$, with the ratio of capillary tip radii, $K^*$, maintained constant at 0.44. The axis on the right-hand side of the plot indicates the measured plug volume. Horizontal error bars indicate slenderness uncertainty as a result of positional inaccuracy. Vertical error bar are a result of uncertainty in the plug volume calculation due to image processing. The results show the expected trend of increased plug volume with liquid bridge slenderness ratio. Decreasing $Q^*$ resulted in a dramatic increase in dimensionless plug volume. Altering $Q^*$ also affected the volume of silicone oil separating the aqueous plugs as $Q^*$ is the oil flowrate as a fraction of the total flowrate. The lowest repeatable volume measured using this particular geometry was approximately 90 nL with $\Lambda^*=0$, $Q^*=0.75$. The highest volume measured was approximately 3.9 μL with $\Lambda^*=2.36$, $Q^*=0.25$.

In flows where the non-wetting fluid, i.e. the aqueous phase, is displaced by wetting fluid, i.e. oil, a thin film of the wetting fluid separates the droplets from the capillary surface. The thickness of the film results from a balance between the oil viscosity, $\eta$, and the interfacial tension, $\sigma_i$. The thickness of the oil film deposited in a capillary of radius r is given by;

$$h=1.34r(Ca^{2/3}). \quad (0.1)$$

The capillary number, Ca, is given by:

$$Ca = \frac{\eta U}{\sigma_i}, \quad (0.2)$$

where U represents the mean velocity of the flow. Equation (0.1) is obeyed if the film is thin enough to neglect geometric forces, h<0.1r, and thick enough to avoid the influence of long range molecular attraction, h>100 nm. Typical oil film thicknesses for plug flow through 400 μm polymeric fluorocarbon internal diameter tubing were calculated to be of the order of 1 μm. This film thickness was too small to resolve with any degree of accuracy from experimental images. The oil film does, however, form a protective coating preventing aqueous reactor fluid from contacting the Teflon tubing. This has the advantage of preventing a mechanism responsible for carryover contamination whereby small droplets may be deposited onto the walls of microchannels. Table 1 below presents two examples of oil-surfactant combinations used to successfully establish protective oil films around flowing droplets. Surfactant additives act to change the interfacial tension between droplets and the oil carrier fluid such as to promote the establishment of a protective oil film, the thickness of which is given by Equation 0.1.

TABLE 1

| Oil | Surfactant | Concentration |
|---|---|---|
| FC40 | 1H,1H,2H,2H-Perfluoro-1-decanol | 2% W/V |
| AS100 Silicone Oil | Triton X-100 | 0.1% V/V in PCR Buffer Solution |

Figure 13:
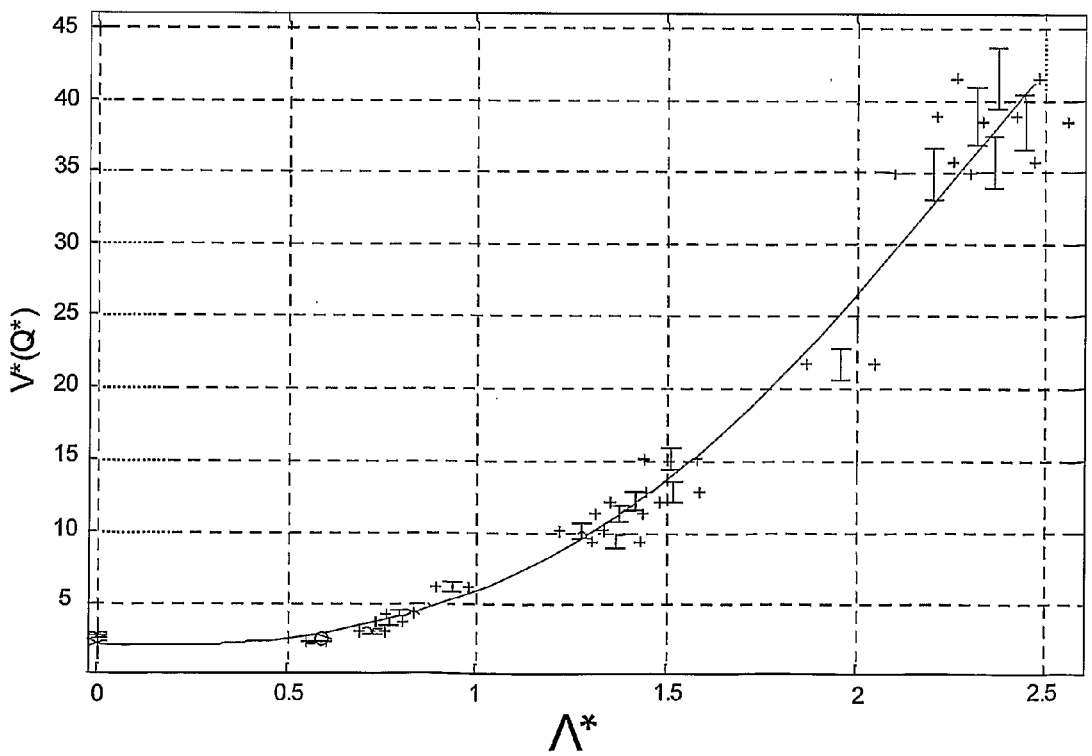
FIG. 13 is a collapsed data characteristic plot for liquid bridge segmentation.

FIG. 13 presents a dimensionless plot of the product of $V^*$ and $Q^*$ versus $\Lambda^*$. The data, taken from the plot shown in FIG. 12, collapsed on to the trend line within the bounds of uncertainty. The data applies to geometries with $K^*=0.44$. Notwithstanding this geometric constraint, the collapsed data does yield, valuable design information. Consider a microfluidic system designer deciding on an appropriate geometry for a segmenting device. The designer will usually know the exact volume to dispense from the outline specification for the device. If there is a sample frequency requirement, the designer may also know a value for $Q^*$. Recalling that $K^*=R_1/R_2$, where $R_1$ and $R_2$ are the inlet and outlet diameters respectively makes the design process relatively easy. Deciding on an arbitrary value for an outlet diameter fixes the aqueous inlet diameter as the data shown in FIG. 15 applies to only to geometries with $K^*=0.44$. With this information in hand, an appropriate value for $V^*(Q^*)$ may be calculated. The corresponding value for $\Lambda^*$ may then be read from the design curve shown in FIG. 13. Finally, $\Lambda^*$ may be used to calculate the tip separation between the inlet and outlet.

Figure 14:
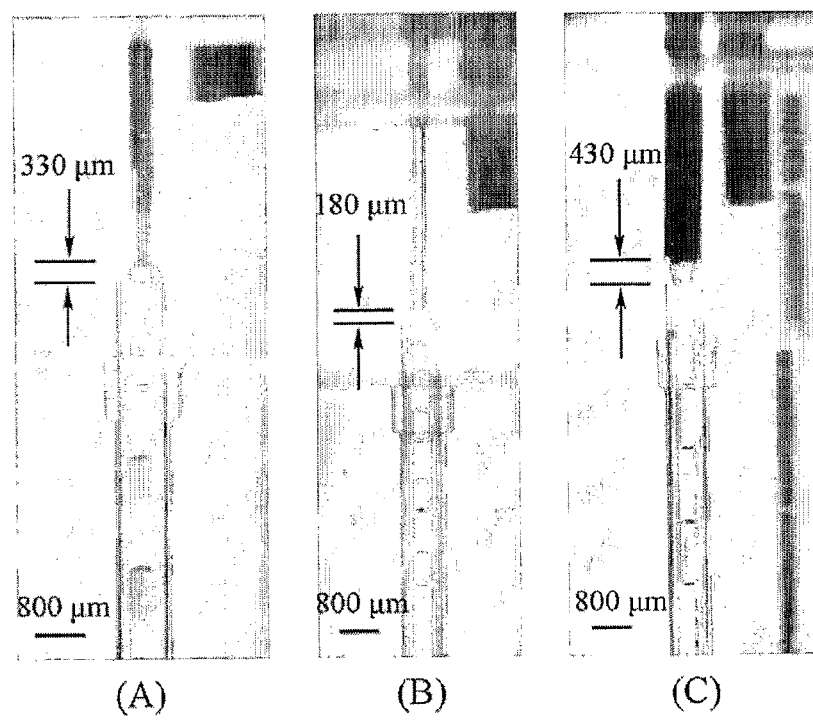
FIG. 14 is a set of photographs of three liquid bridge segmentors having different capillary radii.

As mentioned previously, the data presented in FIGS. 12 and 13 applies to geometries with $K^*=0.44$. The effect of altering $K^*$ on plug volumes dispensed was also investigated. Images of liquid bridge dispensing at three different values for $K^*$ are presented in FIG. 14. Images (A), (B) and (C) correspond to $K^*$ values of 0.25, 0.44 and 1.0 respectively. A $K^*$ value of 0.25 was achieved by assembling a 200 μm fused silica microcapillary at the end of a polymeric capillary tube by a reduction of internal diameter through appropriately sized fused silica. Sealing was ensured with the addition of cyanoacrylate glue at the sleeve interfaces.

Figure 15:
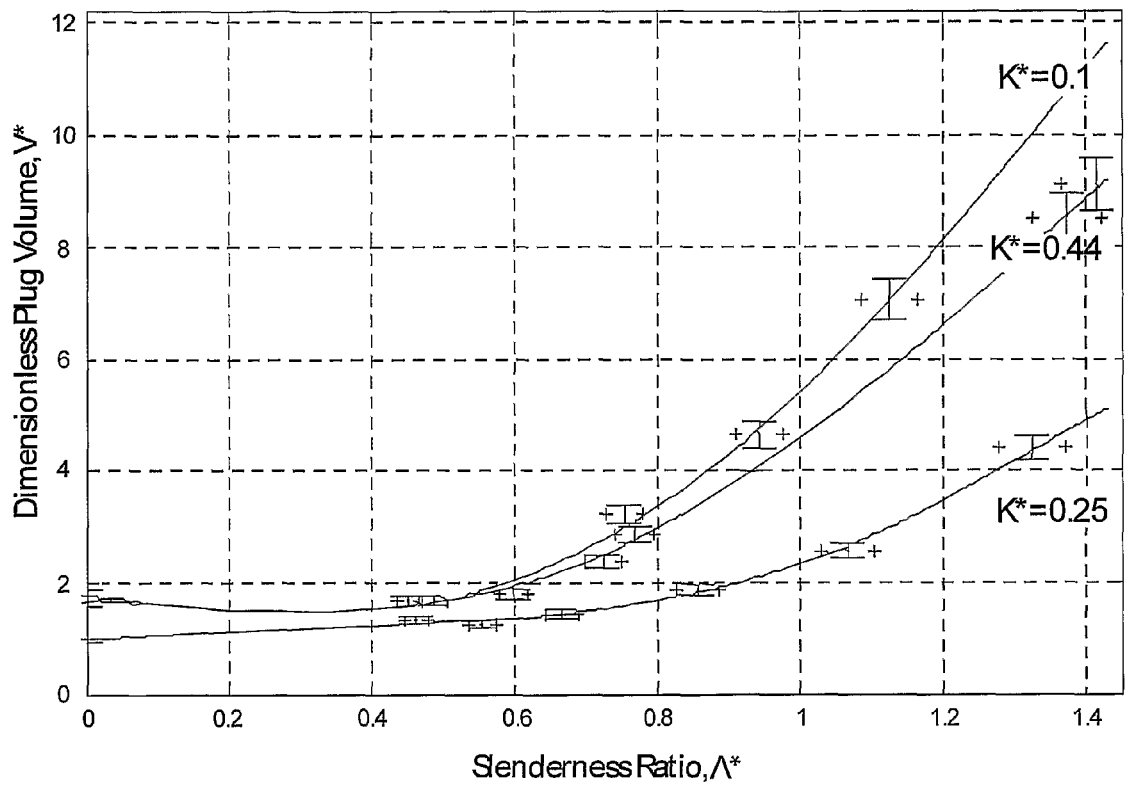

FIG. 15 presents a dimensionless plot of $V^*$ versus $\Lambda^*$ for three different values of $K^*$. The dimensionless plug volume, $V^*$, was scaled with $R_2^3$, and not $R_0^3$ as previously. This permitted a direct comparison of dimensionless plug volumes as $R_2$ remained constant throughout the experiment. It can be seen that decreasing $K^*$ generally lowers the plug volumes dispensed for any given value of slenderness, $\Lambda^*$. The minimum volume dispensed with $K^*=0.25$ was approximately 60 nL whilst that of K*=0.44 and K*=1 was approximately 110 nL. Attempts to collapse the data shown in FIG. 15 onto a single line, similar to the plot shown in FIG. 13, were unsuccessful. This was due to the highly non-linear relationship between K* and V* for any given value of Λ*.

The repeatability with which the liquid bridge dispensing system could deliver fluid was of particular interest. FIG. 16 plots plug volume variation over fourteen measurements for a dispensing system with K*=0.44. The results show mean plug volumes of approximately 120 nL and 56 nL with maximum volumetric variations of ±4.46% and ±3.53% respectively. These volumetric variations compare favourably to commercial available micropipettes which have an uncertainty of ±12% when dispensing 200 nL. The accuracy with which one may dispense using micropipettes, however, is thought to be largely dependant upon user skill. The automation of dispensing systems may therefore be justified as a means of eliminating user-user variability. The volumetric analysis presented in FIG. 16 shows liquid bridge dispensing to be a very repeatable means of continuously dispensing sub-microlitre volumes of fluid.

Referring again to the funicular bridge of FIG. 6 an example is presented in FIG. 17. The bridge consists of two opposing capillaries of the same external diameter. The second inlet part is of a finer capillary orientated at right angles to and situated half-way between the other two capillaries. Constraints on opposing capillary radius and the placement of the third capillary helped to simplify the dimensionless stability study. The investigation also necessitated modifications to the dimensionless parameters characterising axisymmetric liquid bridge geometry. The slenderness ratio, Λ*, was calculated using:

$$\Lambda^* = \frac{\sqrt{L^2 + S^2}}{2R_0}, \quad (1)$$

where L and S correspond to the distances indicated in FIG. 17. $R_0$ is defined as the mean radius, i.e. $(R_1+R_2)/2$. K* is defined as $R_1/R_2$. The volumetric ratio, V*, is defined as:

$$V^* = \frac{\overline{V}}{\pi R_0^2 \sqrt{L^2 + S^2}}, \quad (2)$$

where $\overline{V}$ is the measured volume at which bridge collapse occurs. In terms of the geometry presented in FIG. 17, a funicular bridge collapse corresponds to detachment from the finer capillary.

Figure 18:
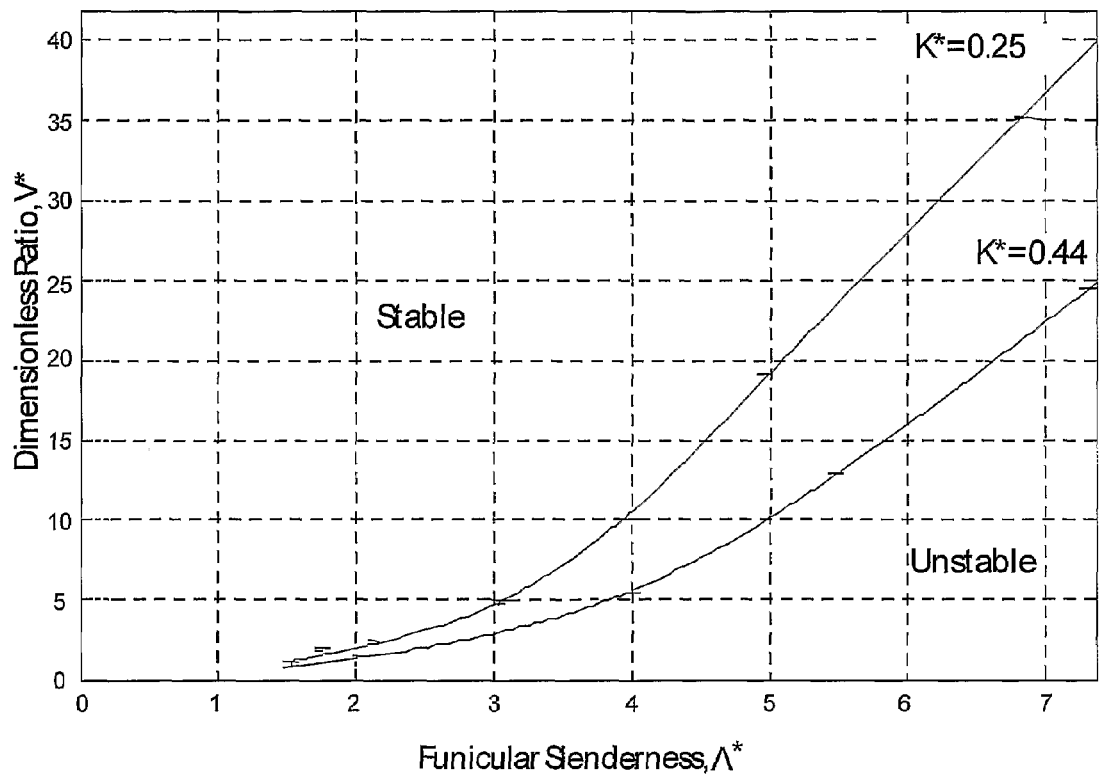
FIG. 18 is a funicular liquid bridge characteristic stability plot.

FIG. 18 shows a stability diagram the approximate location of the minimum volume stability boundary for purified water funicular liquid bridges with a lateral Bond number of 1.25× $10^{-4}$, a near weightless environment. The boundaries of stability were found by fixing a value for Λ*, establishing a stable funicular bridge and withdrawing fluid until the bridge collapsed. The collapse was recorded via a CCD and the frame immediately following rupture was analysed to measure the volume. The calculation of the bridge volume was simplified by the fact that the collapsed funicular bridge exhibited axisymmetry with respect to the axis of the two larger capillaries. Minimum volume stability boundaries are plotted for K*=0.25 and K*=0.44. Lower K* values displayed increased instability. Volumetric data for Λ* values lower than approximately 1.5 was difficult to obtain with the geometry used and so was omitted from the stability diagram.

This is, to the best of the inventor's knowledge, the first experimental study of funicular bridges for this application. The formation of a funicular bridge deemed unstable by the graph shown in FIG. 18 ensures the injection of fluid into an aqueous plug passing through opposing capillaries. A further advantage to using funicular bridge dispensers is based on the speed at which the process takes place. Typical instabilities last of the order of 100 ms, insufficient time for the host droplet fluid to diffuse to the dispensing capillary tip. This is a further preventative measure against carryover contamination.

The two input one output, funicular bridge can be configured so that the expression profile of many genes may be addressed. One input contains the primer and premix in a continuous phase, the outlet then delivers them in droplet form. Firstly many input and output capillaries, say p, can be set in planes perpendicular to that of FIG. 6. A perpendicular arrangement allows for good optical access in the planar thermal cycler which is connected to the output. Each arrangement of two inputs and one output can be used to address a single primer, giving p primers. This, however, would make for a very long device in the plane perpendicular to FIG. 6. If serially variant primers were fed into each input, as described in FIGS. 2 and 8, numbering q, this would reduce the scale. Further, if the primers were multiplexed, to order r, in each droplet the scale would be further reduced. The number of primers that could then be addressed would be:

$$N = p \times q \times r.$$

By this means a PCR test of the whole genome of any living form, including the human, could be addressed, which would have applications beyond diagnosis, in many fields of pure and applied science.

Figure 19:
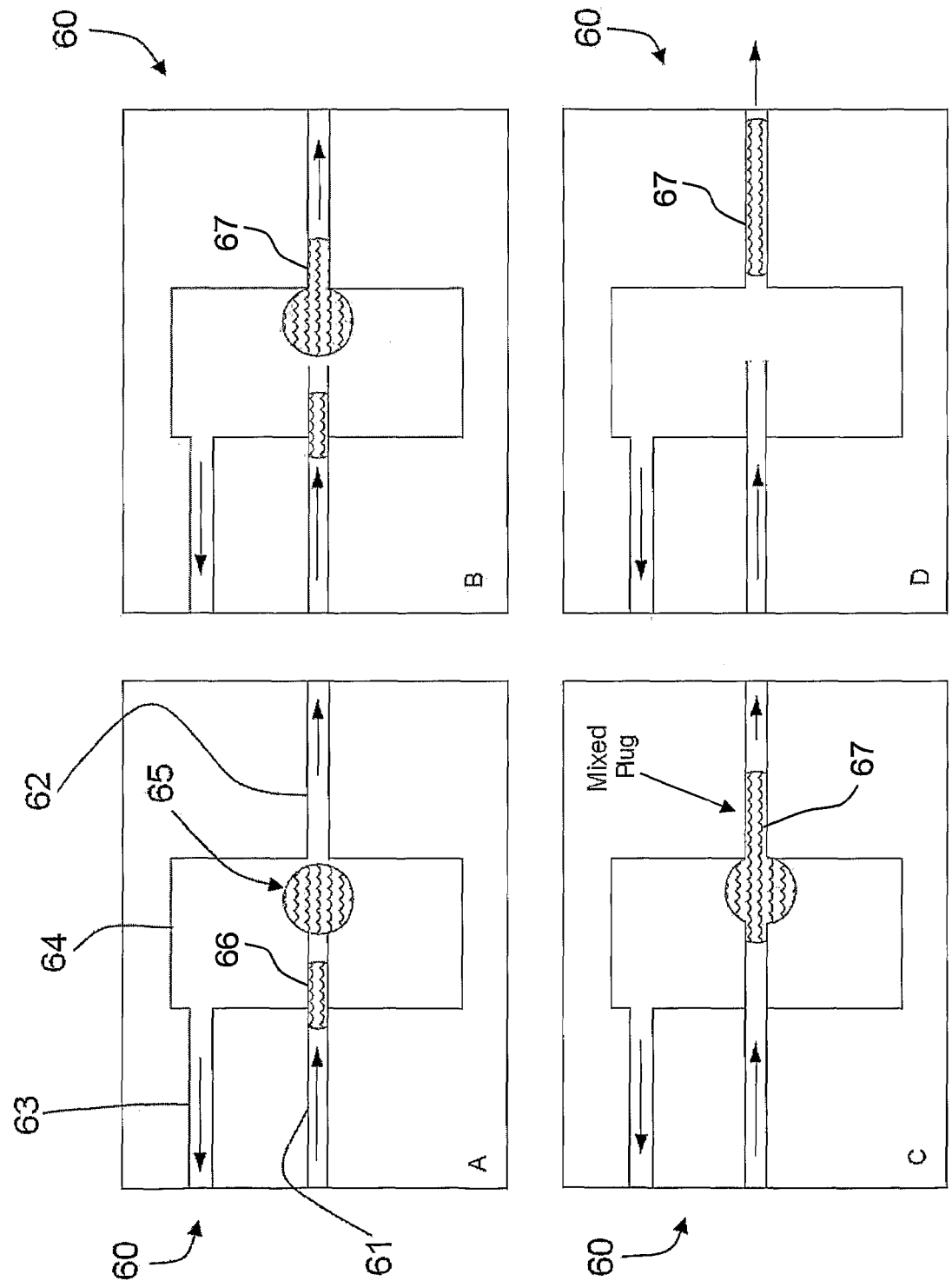
FIG. 19 is a set of diagrams A to D showing operation of an alternative mixer bridge of the invention.

In another embodiment, mixing of droplets may be achieved with only one inlet port and two outlet ports. Inlet droplets are close together, and the delay for droplet formation within the chamber due to a reduction in fluid flow through the main line causes a collision and hence mixing. Such mixing may be caused by withdrawal of oil from the chamber, or upstream of it. Referring to FIG. 19 a bridge 60 has an inlet port 61, an outlet port 62, an oil withdrawal port 63, and a chamber 64. A large leading droplet entering the chamber forms a droplet 65 in the chamber. As oil is withdrawn from the chamber 64 through the oil withdrawal port 63, a smaller trailing droplet collides with the leading droplet bubble 65 so that the mixing occurs. A larger mixed droplet 67 leaves via the outlet port 62.

In more detail, initially, the entire system is primed with a density matched oil. The diameter of the ports 61, 62 and 63 is 200 μm, and is more generally preferably in the range of 150 μm to 400 μm. The spacing between the ports 61 and 62 is c. 1 mm, and is more generally preferably in the range of 0.2 to 1.5 mm. The enveloping oil is controlled to have a pressure of no more than 0.5 to 1.0 bar above atmospheric. The enveloping liquid is silicone oil with a viscosity of 0.08 to 0.1 Pas.

As with the lateral mixing bridge 30 and the segmentation bridge 50, droplets are enveloped by carrier oil entering and exiting the bridge 60 via a protective oil film around the droplets. This provides a non-contacting solid surface that prevents carryover contamination from one droplet to the other. The oil is used as the control fluid and is density-matched with the reactor plugs such that a neutrally buoyant environment is created within the oil chamber 64. When two unmixed droplets arrive at the chamber in series from the inlet port 61, the first droplet assumes a stable capillary-suspended spherical form upon entering the chamber, step A. The spherical shape grows until large enough to span the gap between the ports, forming an axisymmetric liquid bridge, step B. The control outlet port 63 removes a flow of oil from the chamber causing the first droplet to slow and remain as a spherical shape at the outlet port 62 for a longer period. This allows time for the second droplet to form a stable capillary-suspended spherical shape on entering the chamber. With the first droplet formed as a spherical shape at the outlet 62 and the second droplet formed as a spherical shape at the inlet, the droplets can form as one and create an axisymmetric liquid bridge, step C. The mixed droplet then exits through the outlet port 62, step D.

The flow conditions most be matched so that the flow through the inlet 61 is greater than the flow out of the control outlet port 63. A typical flow in through the inlet is typically 5 μl/mn and more generally in the range of 2 to 7 μl/mn. The flow away from the chamber through the control port 63 is typically 2.5 μl/mn and more generally in the range of 1 to 5 μl/mn. Since there is conservation of mass flow within the bridge, this means that the flow through the outlet port 62 will balance the bridge to give a flow of typically 2.5 μl/mn and more generally in the range of 1 to 5 μl/mn.

This serial mixing bridge 60 can be used with a constant outlet flow through the control port 63. In doing so not only will droplets be mixed but also the fluid flow through the system can be decreased. In addition, this bridge 60 can be used in conjunction with a sensor to time the withdrawal of fluid through the control port 63 so as to maintain the main fluid flow at a generally constant flowrate. The sensor used can be a droplet detection sensor which comprises of a LED and photodiode. The LED is projected directly onto the centre of the tube. A photodiode is positioned directly opposite the LED to pick up the light refracted through the tube. As a droplet of varying properties to that of oil flows past the LED and photodiode, the light refracted through the liquid is altered slightly. This slight alteration is detected by the photodiode in the form of a change in voltage. This change in voltage can be used to time the control flow through outlet port 63. The serial mixing bridge 60 can also be used downstream of the lateral mixing bridge 30. In doing so, the system can compensate for droplets that have not yet mixed after flowing through the lateral mixer 30. The reason for droplets not mixing may be that the droplets are out of phase with each other and have not met simultaneously at the lateral mixing bridge 30. Another system of ensuring mixing has occurred is to include a droplet detection sensor with the serial mixing bridge 60 downstream of the lateral mixing bridge 30. If the droplet detection senses two droplets in unusually quick succession then the droplets have not yet mixed. The droplet detection sensor can then switch on the serial mixer 60 and mix the two droplets.

It will be appreciated that the invention provides for particularly effective processing of droplets for applications such as amplification of nucleic acids. It provides particularly effective mechanisms for mixing of droplets and for segmenting long droplets or plugs.

The invention is not limited to the embodiments described but may be varied in construction and detail. For example, the sample liquid may be delivered continuously to an inlet port in some embodiments, for segmentation. In this case the same basic mechanism provides droplets of a controlled size in to the outlet port. Also, the flow controller may merely be a passive feed system based on gravity or indeed capillary action rather than an active pumping means such as an infusion pump.

The invention claimed is:

1. A method of controlling operation of a liquid bridge, comprising:
    directing flow of a first sample fluid and a second sample fluid and a carrier fluid into a liquid bridge,
    controlling the flow of the first sample fluid and the second sample fluid so that droplets of the first sample fluid and the second sample fluid mix within the liquid bridge,
    such that the first sample fluid and the second sample fluid forms a droplet wrapped in the carrier fluid prior to entering an outlet of the liquid bridge.

2. The method according to claim 1, wherein the flow is controlled to cause segmentation of a continuous stream or large droplets of the sample fluid in a chamber of the liquid bridge to provide a sequence of segmented sample droplets derived from the sample fluid entering the liquid bridge.

3. The method according to claim 1, wherein the first and second sample fluids are delivered to different inlets of the liquid bridge, the inlets being located so that droplets of the first sample fluid and the second sample fluid mix to form a single mixed droplet that exists via the outlet of the liquid bridge.

4. The method according to claim 1, wherein the first and second sample fluids are delivered to the liquid bridge in a single inlet as successive droplets, and flow is controlled so that the droplets collide within a chamber of the liquid bridge to mix.

5. The method according to claim 4, wherein the carrier fluid from between the first and second sample droplets is withdrawn before the droplets enter the liquid bridge, resulting in the droplets colliding within the chamber.

6. A method of segmenting a liquid sample, the method comprising:
    delivering a droplet in a continuous stream or large droplets to an inlet of a first delivery channel aligned with an first outlet of a second delivery channel and an second outlet of a third delivery channel;
    controlling the flow of the droplet so that the sample periodically bridges the inlet and the first outlet and the second outlet, whereby a first segmented droplet is delivered to the first outlet and travel via the second delivery channel and a second segmented droplet is delivered to the second outlet and travel via the third delivery channel;
    wherein the first segmented droplet and the second segmented droplet travel in a flow of an immiscible carrier fluid and the inlet and the first output and the second output are in fluid communication with the carrier fluid.

7. A method of conducting a chemical reaction, the method comprising
    a) segmenting a sample using the method of claim 6; and
    b) conducting a chemical reaction in the segmented sample.

* * * * *